United States Patent [19]

Hall et al.

[11] Patent Number: 5,750,408

[45] Date of Patent: May 12, 1998

[54] METHOD OF MODIFYING AN AUTOMOTIVE TYPE OXYGEN SENSOR FOR USE IN AN INDUSTRIAL PROCESS ANALYZER

[75] Inventors: George R. Hall, Geneva; Daniel C. Barnett, Concord; Robert A. Smith, Mentor; Scotty Y. Jewett, Lyndhurst, all of Ohio

[73] Assignee: Elsag International B. V., Netherlands

[21] Appl. No.: 840,261

[22] Filed: Apr. 14, 1997

Related U.S. Application Data

[63] Continuation of Ser. No. 604,193, Feb. 21, 1996, abandoned, which is a continuation of Ser. No. 906,713, Jun. 30, 1992, abandoned.

[51] Int. Cl.$^6$ .................................................. G01N 25/00
[52] U.S. Cl. .......................... 436/137; 436/138; 436/143; 436/149; 436/151; 436/155; 422/94; 422/95; 422/98; 204/428
[58] Field of Search ........................... 436/137, 138, 436/143, 149, 151, 155; 422/94, 95, 98; 204/428

[56] References Cited

U.S. PATENT DOCUMENTS

| | | | |
|---|---|---|---|
| 3,960,693 | 6/1976 | Weyl et al. | 204/428 |
| 4,141,813 | 2/1979 | Kita et al. | 204/428 |
| 4,152,232 | 5/1979 | Ohsuka et al. | 204/428 |
| 4,159,234 | 6/1979 | Eifler et al. | 204/428 |
| 4,466,880 | 8/1984 | Torii et al. | 204/428 |
| 4,507,192 | 3/1985 | Ebizawa et al. | 204/428 |
| 4,526,672 | 7/1985 | Reed | 204/428 |
| 4,588,493 | 5/1986 | Blumenthal | 204/410 |
| 4,591,422 | 5/1986 | Kato et al. | 204/426 |
| 4,624,770 | 11/1986 | Yamada et al. | 204/428 |
| 4,664,886 | 5/1987 | Novack et al. | 422/94 |
| 4,668,477 | 5/1987 | Nishio et al. | 422/98 |
| 4,717,464 | 1/1988 | Oshima et al. | 204/427 |
| 4,756,885 | 7/1988 | Raff et al. | 422/98 |
| 4,835,108 | 5/1989 | Cooper | 436/137 |
| 4,875,990 | 10/1989 | Kodachi et al. | 204/408 |
| 4,883,643 | 11/1989 | Nishio et al. | 422/94 |
| 4,897,174 | 1/1990 | Wang et al. | 204/425 |
| 4,915,815 | 4/1990 | Shibata et al. | 204/429 |
| 4,929,331 | 5/1990 | Kato et al. | 204/426 |
| 4,944,861 | 7/1990 | Reber | 204/428 |
| 4,956,072 | 9/1990 | Kojima et al. | 204/424 |
| 4,957,705 | 9/1990 | Uchikawa | 422/94 |
| 4,986,892 | 1/1991 | Kato et al. | 204/427 |
| 5,012,670 | 5/1991 | Kato et al. | 73/31.05 |
| 5,037,526 | 8/1991 | Kato et al. | 204/428 |
| 5,037,761 | 8/1991 | Barnett et al. | 436/137 |
| 5,049,255 | 9/1991 | Wolfe et al. | 204/428 |
| 5,071,626 | 12/1991 | Tuller | 422/98 |
| 5,089,133 | 2/1992 | Kato et al. | 204/427 |
| 5,137,616 | 8/1992 | Poor et al. | 204/428 |

Primary Examiner—Milton Cano
Attorney, Agent, or Firm—Vytas R. Matas

[57] ABSTRACT

In an oxygen analyzer for an industrial process, an automotive type oxygen sensor has a sensor element assembly with an outer thin walled shield containing insulation and surrounding the sensor element of the automotive type oxygen sensor.

5 Claims, 2 Drawing Sheets

METHOD OF MODIFYING AN AUTOMOTIVE TYPE OXYGEN SENSOR FOR USE IN AN INDUSTRIAL PROCESS ANALYZER

This is a continuation of application Ser. No. 08/604,193 filed Feb. 21, 1996 abandoned which is a continuation of application Ser. No. 07/906,713 filed Jun. 30, 1992, abandoned.

FIELD AND BACKGROUND OF THE INVENTION

The present invention relates in general to oxygen sensors, and in particular to a new and useful sensor for use in harsh environments.

U.S. Pat. No. 5,037,761 ("the '761 Pat.") discloses the use of an automotive type oxygen sensor for sensing oxygen in an industrial process analyzer.

The use of oxygen sensors for measuring oxygen concentrations in natural gas fired processes is known. When such sensors are used for processes fired with coal or other dirty fuels, errors in accuracy occur due to $SO_2$, $NO_x$ and other combustion by-products. The $SO_2$, $NO_x$ and other combustion by-products contaminate the sensing element of the oxygen sensor giving rise to calibration shifts, reduced span (by as much as 35%) and other problems.

In order to minimize the problems described above, it is desirable to increase the operating temperature of the sensor. One approach to increasing the sensor operating temperature was to increase the voltage to the heater inside the sensor. This increase in voltage minimized the problems described above, but resulted in severe reductions in heater life. Therefore, it was desirable to modify the oxygen sensor to thereby increase its operating temperature without decreasing the life of the heater.

The use of prior art oxygen sensors in an industrial process analyzer may give rise to an undesirable flashback when the process is ignitable. Therefore, it is desirable that the modification to the oxygen sensor which increases the temperature of the sensor without decreasing its heater life also act as a flash arrestor to thereby prevent flashback.

SUMMARY OF THE INVENTION

According to the present invention, an automotive type oxygen sensor is modified by removing its relatively thick protective shield and replacing it with an extremely thin protective shield having a selected number of small holes to control the diffusion rate of gas into the sensor. The inside of the thin shield is filled with a ceramic insulation material of controlled weight and density so as to increase the temperature on the outside surface of the sensor. The thin shield helps to maintain the heat provided by the sensor heater at the sensor to thereby assist in the increase of the operating temperature on the outside surface of the sensor.

The foregoing modifications were found to be effective against calibration shifts (offsets) while maintaining a broad measurement span and long useful life of the sensor. The modifications stabilized the sensor output and reduced the errors caused by $SO_2$, $NO_x$ and other combustion by-products. We believe that the modifications also act as a flash arrestor for preventing flashback into an ignitable process.

Accordingly an object of the present invention is to provide an oxygen content analyzer for gas of an industrial process, the analyzer comprising an automotive type oxygen sensor having a sensor element in an analyzer manifold, the automotive type oxygen sensor having a sensor element assembly and electric heating means, the improvement comprising: a thin-walled perforated shield with or without insulation, forming an outer wall of the oxygen sensor assembly, the sensor element spaced inwardly of said shield and connected to the automotive type oxygen sensor, whereby calibration shifts due to contamination by $SO_2$, $NO_x$ and other combustion by-products in the industrial process are avoided. The improvement may further comprise insulation in said shield and around said sensor element.

A further object of the present invention is to provide an alternative improvement to the oxygen sensor to avoid calibration shifts wherein the sensor element is protected using any porous material such as ceramic, with or without insulation.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in a which a preferred embodiment of the invention is illustrated.

DESCRIPTION OF THE PREFERRED EMBODIMENTS

Figure 1:
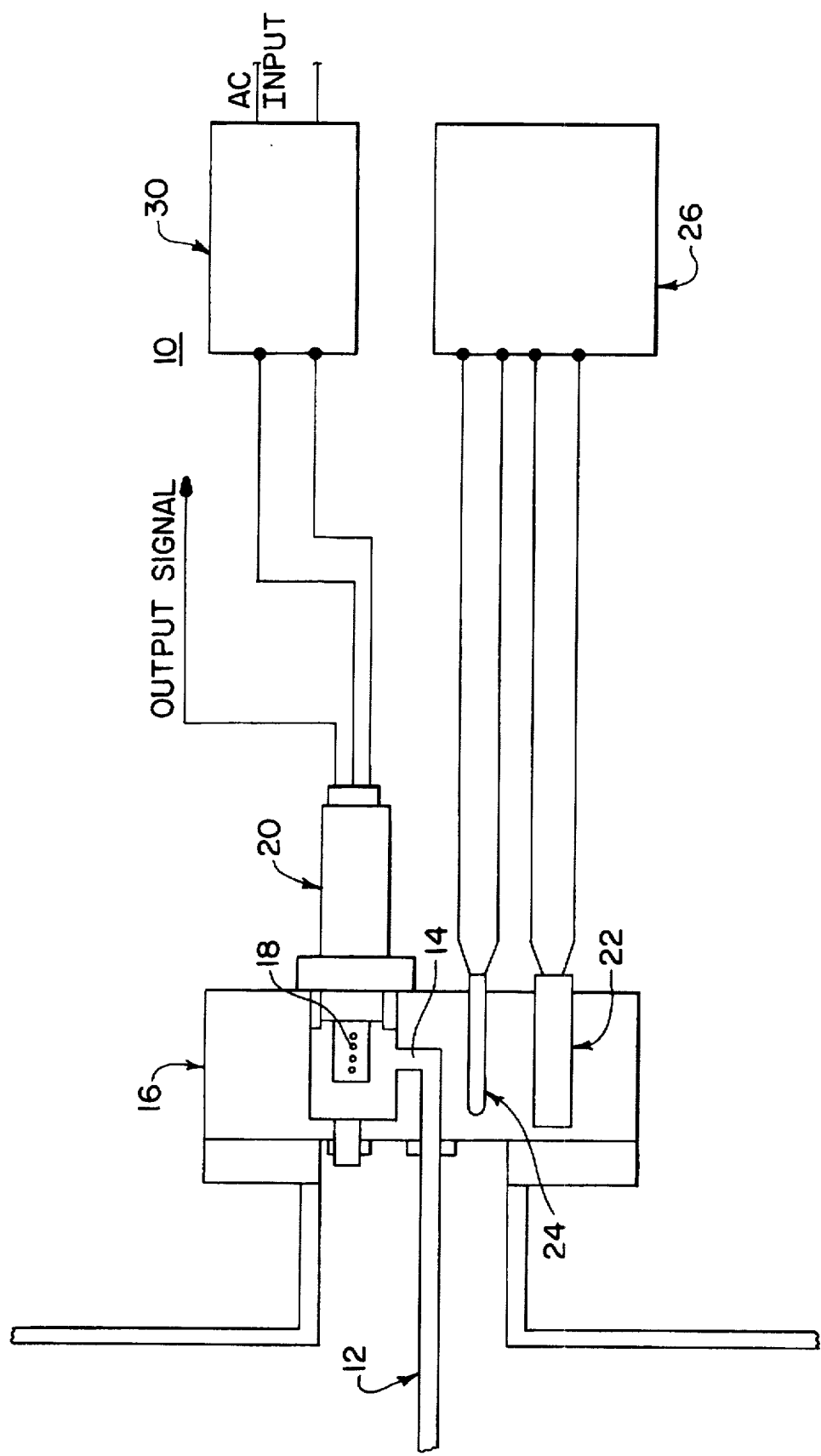
FIG. 1 is a schematic diagram showing the use of an automotive type oxygen sensor in conjunction with an associated power supply to analyze the oxygen content of a gas in an industrial process.

FIG. 1 is a schematic diagram of a system 10 for analyzing the oxygen content of an industrial process by using an automotive type oxygen sensor 20 and is identical to FIG. 1 of the '761 Patent. In system 10, a gas sample is drawn from the monitored industrial process through a sample probe 12. The drawing of the sample is typically accomplished through the use of an air powered aspirator (not shown) within the system 10. The gas sample is directed through a passageway 14 in the analyzer manifold 16 across a sensor element assembly of the automotive type oxygen sensor 20 and is exhausted back into the gas flow within the industrial process. The analyzer manifold 16 is controlled at a substantially constant temperature above the gas stream dew point, typically 300° to 400° F. (149° to 204° C.). The controlled manifold temperature provides a substantially constant ambient temperature for the automotive type oxygen sensor 20.

The analyzer manifold 16 is heated by heaters 22 A temperature sensing element 24 is connected to a temperature control circuit 26. Circuit 26 provides the voltage to heaters 22. An integral heater (not shown) within the automotive type oxygen sensor 20 is connected to a power supply 30 which is manually adjusted to provide the desired operating temperature at the sensor element assembly 18 of the automotive type oxygen sensor 20. For the environment in which the sensor of the '761 Patent is typically used, the operating temperature of the sensor element 18 is in the range of about 1300° to 1400° F. (704° to 760° C.). Additional details concerning the operation of the analyzer are disclosed in the '761 Patent which is incorporated herein by reference.

Figure 2:
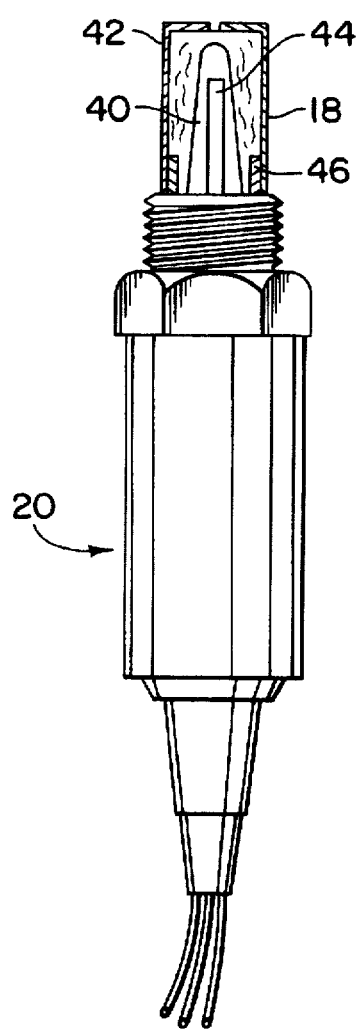
FIG. 2 is a side elevational view of the automotive type oxygen sensor with portions in section.

As was described above, when the analyzer disclosed in the '761 Patent is used for processes fired with coal or other dirty fuels, errors in accuracy occur due to $SO_2$, $NO_x$, and other combustion by-products contaminating the sensor element shown as 40 in FIG. 2 and forming part of the sensor assembly 18. As was also described above, one approach to minimize the occurrence of accuracy errors is to increase the voltage to the heater inside the sensor described in the '761 Patent to thereby increase the sensor operating temperature to a range of about 1450° to 1550° F. (788° to 843° C.). This increase in voltage and therefore this increase in temperature minimized the occurrence of accuracy errors, but resulted in increased heater failure.

The present invention makes the sensor more efficient, minimizes the occurrence of the accuracy errors and allows the operating voltage to the heaters 22 to be reduced thereby increasing the life of the sensor. In the embodiment for the sensor system 10 described herein, the voltage to the heaters 22 was reduced from the 18 volts used with the sensor of the '761 Patent to 17 volts. It is the invention described herein which allows the reduction in voltage without causing the operating temperature of the sensor element 18 to fall below the lower limit of the 1450° to 1550° F. operating range. The end result is that the errors caused by $SO_2$ and $NO_x$ and other combustion by-products are now less than two percent (2%).

Figure 3:
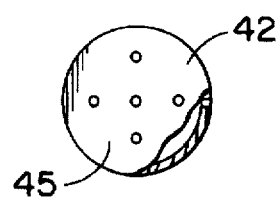
FIG. 3 is a top plan view with a portion cut away for the shield of the sensor assembly of the present invention.
Figure 4:
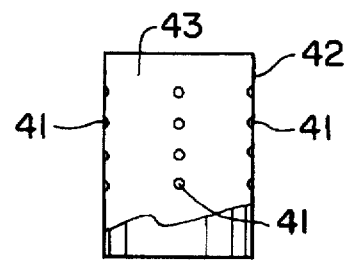
FIG. 4 is a side elevational view of the shield, with a portion cut away.

In accordance with one embodiment of the present invention, the usual shield provided around the sensor element is replaced with a thin-walled perforated shield 42 (see FIGS. 2 to 4). The shield 42 is cylindrical in shape and has an outer diameter of about 0.499 to 0.512 inches (12.67 to 13.00 mm) and a height of about 0.685 to 0.695 inches (17.4 to 17.65 mm).

Shield 42 has a pattern of perforations best shown in FIGS. 3 and 4 which provide free flow of gas into and out of the shield. The interior of the shield is packed with fibers or other permeable insulation material 44 for example, KAOWOOL material available from Babcock and Wilcox. The wall thickness of the top of the shield is preferably about 0.015 to 0.020 inches (0.38 to 0.51 mm). The inside diameter of the shield is preferably 0.467 to 0.470 inches (11.86 to 11.94 mm).

In the embodiment shown in FIGS. 2 to 4, the shield has a total of 21 holes. Each hole has a diameter of about 0.045 inches (1.14 mm). There are four columns 41 of four holes each arranged essentially symmetrically about the outside surface 43 of shield 42. Three of these columns are shown in FIG. 4. Vertical spacing between the holes in each column 41 is advantageously about 0.1 inches (2.54 mm).

On the top 45 of shield 42 shown in FIG. 3, four holes are provided in a circle around a central hole. The circle has a diameter of about 0.280 inches (7.11 mm).

Advantageously, the shield is fabricated from number 303 stainless steel. The automotive oxygen sensor 20 may be a stock item provided by the Bosch Company, such as number 9F-472, and is primarily used in vehicles manufactured by the Ford Motor Company.

As shown in FIG. 2, the preexisting neck 46 in the sensor element assembly is cut off to a height of about 0.140 to 0.150 inches (0.36 to 0.38 mm) and provides the seat for the shield. The shield does not have any perforations up to about 0.250 inches (0.64 mm) above the lower end of the shield where the first set of perforations start.

An alternate embodiment of the invention is to provide a different number of diffusion holes through a different shield made of the same material as the shield described above or another material such as ceramic or other non-metals. The shield may have different shape than the cylindrical shape or a different hole pattern than the shield shown in FIGS. 2 to 4. The shield may also be fabricated from any porous material, such as ceramic, with or without any insulation therein.

Figure 5:
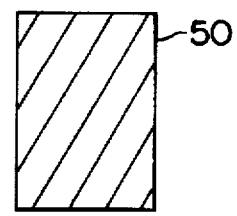
FIG. 5 is a side elevational view of a ceramic shield.
Figure 6:
FIG. 6 is a top plan view of the ceramic shield.

One example of an alternate embodiment is the ceramic shield 50 having the KAOWOOL material 44 therein which is shown in FIGS. 5 and 6.

The following table shows in the first row the sensor temperature and heater temperature obtained from the sensor described in the '761 Patent ("Standard Sensor") with the voltage of the heaters 22 set at 18 VDC and 19 VDC. The table shows in the second row the sensor temperature and heater temperature obtained from a sensor embodied in accordance with the embodiment of the present invention shown in FIGS. 2 to 4 having a shield insulated with 0.34 to 0.36 grams of KAOWOOL material with the heaters voltage set at 17 VDC, 18 VDC and 19 VDC. The table shows in the third row the sensor temperature and heater temperature obtained from a sensor embodied in accordance with the embodiment of the present invention shown in FIGS. 2 to 4, but without any insulation, for a heaters voltage of 18 VDC.

TABLE

| SENSOR TEMPERATURE/HEATER TEMPERATURE | | | |
|---|---|---|---|
| SENSOR | SENSOR HEATER VOLTAGE | | |
| CONFIGURATION | 17 VDC | 18 VDC | 19 VDC |
| STANDARD | — | 1417/1947 | 1473/2044 |
| PERFORATED METAL SHIELD AND INSULATION | 1501/1936 | 1554/2032 | 1633/2134 |
| METAL SHIELD ONLY | — | 1507/1940 | — |

| | |
|---|---|
| Initial Testing: | 18 VDC and standard sensor. Heater life OK, but sensor temperature too low for good performance in a harsh environment. |
| 2nd Round: | 19 VDC and standard sensor. Sensor performance good but heater life too short. |
| 3rd Round: | 18 VDC and modified sensor. Sensor performance good but heater life too short (even though only 18 VDC). |
| Final Round: | 17 VDC and modified sensor. Sensor temperature still high enough for good performance and heater temperature low enough for good life. |

What is claimed is:

1. A method of modifying a shielded automotive sensor assembly having an integral heater to heat the sensor to a range of 1300° F. to 1400° F. in response to a predetermined elevated voltage applied to the heater to have the automotive sensor act as an industrial process oxygen sensor comprising the steps of:

replacing the automotive oxygen sensor shielding with a thin wall shield;

packing a space between said thin wall shield and the sensor with an insulating material;

lowering the voltage to the automotive sensor heater below the predetermined elevated voltage to approximately 17 VDC; and providing predetermined perforations in the thin wall shield to allow a predetermined free flow of gas through said packing and to the sensor which will raise and maintain the sensor temperature above 1450° F. while lowering the operating temperature of said heater below its usual operating temperature without said predetermined perforations at said lower voltage thus minimizing combustion by-product errors and calibration shifts while increasing the life of the sensor.

2. A method as set forth in claim 1 where said insulting material is a ceramic fiber insulation.

3. A method as set forth in claim 1 wherein said thin wall shield is made from a porous ceramic material.

4. A method as set forth in claim 1 wherein said thin wall shield comprises number 303 stainless steel having four columns of four holes each arranged symmetrically about the outside surface of the shield and four holes circularly arranged along the top of the shield.

5. In a method of modifying a shielded automotive sensor assembly having an integral sensor shield and heater operating at approximately 1947° F. to heat the sensor to approximately 1417° F. in response to a predetermined elevated voltage of approximately 18 VDC applied to the heater to thus have the automotive sensor act as an industrial process oxygen sensor for harsh environments comprising coal combustion processes which require the oxygen sensor to operate above 1500° F. for extended periods of time the improvement comprising the steps of:

replacing the normally found automotive oxygen sensor shielding with a thin wall shield having packing between the sensor and said thin wall shield;

lowering the voltage to the automotive sensor heater to approximately 17 VDC; and providing predetermined perforations in the thin wall shield to allow a predetermined free flow of gas through said thin wall shield and packing to the sensor which will raise and maintain the sensor temperature above 1500° F. while lowering the operating temperature of said heater below its operating temperature at 18 VDC with the normally found shield to thus minimizing combustion by-product errors and calibration shifts while increasing the life of the sensor.

* * * * *